United States Patent [19]

Otani et al.

[11] Patent Number: 4,584,400
[45] Date of Patent: Apr. 22, 1986

[54] REFINING PHENYLALANINE

[75] Inventors: Masaru Otani, Kawasaki; Chiaki Sano, Tokyo; Isao Kusumoto, Saga, all of Japan

[73] Assignee: Ajinomoto Co., Inc., Tokyo, Japan

[21] Appl. No.: 678,809

[22] Filed: Dec. 6, 1984

[30] Foreign Application Priority Data

Dec. 26, 1983 [JP] Japan ................................ 58-251035

[51] Int. Cl.[4] .............................................. C07C 45/79
[52] U.S. Cl. ...................................... 562/443; 435/108
[58] Field of Search .......................... 435/108; 562/443

[56] References Cited

U.S. PATENT DOCUMENTS 3,909,353  9/1975  Tsuchido et al. .................... 435/108

FOREIGN PATENT DOCUMENTS 27874    5/1981  Fed. Rep. of Germany ...... 562/443
45-860  12/1970  Japan .................................. 562/443
53-96388 8/1978  Japan .................................. 435/108

OTHER PUBLICATIONS

Sannomiya et al., Chem. Abst., vol. 99, #28491d (1983).
Szente et al., Chem. Abst., vol. 95, #185,787q (1981).
Specht et al., Chem. Abst., vol. 97, #188,140a (1982).
Belikov et al., Chem. Abst., vol. 81, #136,527g (1974).
Kreindlin et al., Chem. Abst., vol. 98, #143,810 (1982).
Kyowa, Chem. Abst., vol. 93, #168,613w (1980).

Primary Examiner—James H. Reamer
Attorney, Agent, or Firm—Oblon, Fisher, Spivak, McClelland & Maier

[57] ABSTRACT

A process for refining phenylalanine, in which a phenylalanine solution containing tyrosine as the main impurity and other impurities is contacted with a non-polar, highly porous synthetic adsorbent, adsorbing phenylalanine on the adsorbent selectively, and eluting and recovering the adsorbed phenylalanine, is disclosed.

10 Claims, No Drawings

REFINING PHENYLALANINE

DETAILED EXPLANATION OF THE INVENTION

This invention relates to a new process for refining phenylalanine. It is concerned with a process for eliminating impurities such as tyrosine as the main impurity, amino acids, organic acids, and salts, which are admixed in phenylalanine solution.

The above-mentioned phenylalanine solution is as follows; L-phenylalanine fermentation liquid containing L-tyrosine, intermediate process liquid in order to recover L-phenylalanine from such fermentation liquid, dissolved liquid of the crude crystals of L-phenylalanine containing L-tyrosine obtained from such an intermediate process liquid and other phenylalanine solution containing at least tyrosine as impurities and possibly containing other amino acids, salts, etc. and the process of the present invention may be applied to any L-phenylalanine solution.

The present invention is further illustrated by L-phenylalanine fermentation liquid, wherein various by-producted amino acids, etc. can be easily separated from the L-phenylalanine by recrystallization, etc., while the L-tyrosine has been hardly separable from the L-phenylalanine by a conventional refining process such as recrystallization process and refining process through ion-exchange resin. Refer to Japanese patent publication No. 3789/ '58.

As the result of intensive and extensive studies, the present inventors have found it capable to refine phenylalanine by extremely simple operations. According to the invention, the process of separating and refing phenylalanine from a phenylalanine solution containing tyrosine as the main impurity needs only contact of the solution with a non-polar, highly porous synthetic adsorbent made of styrene-divinyl benzene etc.

The present invention is concerned with a process for obtaining a highly pure phenylalanine solution by contacting a phenylalanine solution containing tyrosine, etc. with a non-polar highly porous synthetic adsorbent, adsorbing only the phenylalanine on the said resin, and then eluting the phenylalanine adsorbed on the resin by a proper solvent. As occasion demands, by concentrating this phenylalanine solution, highly pure phenylalanine crystals can be obtained.

As for the contact manner of a phenylalanine solution with an adsorbent, the batch type and column type are available, and, however, it is better to execute this invention in accordance with a chromatography process of a column type. For instance, by filling the column with a non-polar, highly porous synthetic adsorbent and then passing a phenylalanine solution containing impurities such as tyrosine downward through the column, the adsorbent adsorbs phenylalanine selectively, while the other admixtures can be eliminated as effluent, completely.

Moreover, the concentration of a phenylalanine solution is not particularly critical, and it would be agreeable if only within the saturated solubility at the operation temperature of adsorption. The pH of a phenylalanine solution, considering that the quantity of adsorption reaches a maximum at the isoelectric point, can be maintained between approx. 3 and 9, preferably approx. 5 and 6. Moreover, the upper limit of the operation temperature of adsorption will depend upon the heat-resistance of the adsorbent, because phenylalanine is stable even at high temperatures. The operation temperature of adsorption according to the heat-resistance of the adsorbent, for instance, may be kept below 60° C. or within the range between 0° and 90° C. Even within this range of temperature, as the quantity of the adsorption is varied in such a way that, for example, the quantity of the adsorption of phenylalanine on the adsorbent may reach a maximum around 30° C., the advantageous adsorption operation temperature should be selected according to the preliminary experiment.

Furthermore, in case the concentration of salts ($Na_2SO_4$, NaCl, $NH_4Cl$, etc.) in a phenylalanine solution increases, the adsorption quantity of phenylalanine to the adsorbent also increases, so the adsorption may favorably be operated in accordance with a column system after these salts are added to the phenylalanine aqueous solution (See Example 2).

As for hereupon mentioned non-polar, highly porous synthetic adsorbents, Diaion HP 10 to 50, SP-207 (Mitsubishi Chemical Industries, Ltd.), XAD-2, XAD-4 (Rohm & Haas Co., Ltd.), etc. can be utilized, however, it is to be clearly understood that the adsorbents are not limited to these, therefore, any other non-polar, highly porous synthetic adsorbent made of styrene divinyl benzene having the same properties as these can be used.

Since these non-polar, highly porous synthetic adsorbent have a stronger affinity to phenylalanine than to tyrosine, if, irrespective of the quantity of tyrosine as the main impurity, the adsorption is operated in order to attain the saturated adsorption of phenylalanine, perfectly phenylalanine recovered by the elution will not contain tyrosine. The saturation of the adsorption relating to phenylalanine depends upon the desired purity of phenylalanine.

The elution for the recovery of phenylalanine adsorbed on the non-polar, highly porous synthetic adsorbent is not particularly hard to operate. For instance, the elution of phenylalanine can be easily performed by water, acid, alkali, lower aliphatic alcohol (that is to say, an aqueous solution such as methanol, ethanol, isopropyl alcohol, etc.) and these mixed solution.

EXAMPLE 1

A 2.5 l (pH=6.0) aqueous solution containing 3 g/dl of L-phenylalanine and 40 mg/dl of L-tyrosine was passed through a 1000 ml (80 cm height and 4 cm diameter bed) non-polar, highly porous synthetic adsorbent, SP-207, according to the column system with a condition of SV=1, when L-phenylalanine was adsorbed selectively.

Then, L-phenylalanine was eluted by water as elution solvent (SV=2, SV; the space velocity in elution). Consequently, the quantity of water required for the elution was 20 l, and more than 98 % of L-phenylalanine adsobed proved to be eluted.

By depositing crystals by the concentration of the eluate, 65 g of L-phenylalanine crystals not containing any L-tyrosine, etc. were obtained. The purity of these crystals is more than 99.5 %, furthermore, and no L-tyrosine was detected by T.L.C. (thin layer chromatography) analysis.

EXAMPLE 2

A 3.5 l (pH=5.0) L-phenylalanine solution containing 3 g/dl of L-phenylalanine, 40 mg/dl of L-tyrosine, 100 mg/dl respectively of L-glutamic acid, L-alanine and L-lysine, 10 g/dl of NaCl and 2 g/dl of $Na_2SO_4$ was passed through a 1000 ml (80cm height and 4 cm diameter bed) non-polar, highly porous synthetic adsorbent, XAD-4, according to a column system with a condition of SV=1, when L-phenylalanine was adsorbed selectively.

Then, the L-phenylalanine was eluted by 1 % (v/v) EtOH aqueous solution (SV=4). The quantity of 1 % (v/v) EtOH aqueous solution required for the elution was 14l, and more than 98 % of L-phenylalanine adsorbed proved to be eluted.

By depositing crystals by the concentration of the eluate, 80 g of L-phenylalanine crystals not containing any L-tyrosine, etc. were obtained. The purity of these crystals was more than 99.5 %, furthermore, and no L-tyrosine or other amino acids were detected by T.L.C. analysis.

EXAMPLE 3

A 3.5l (pH=5.0) L-phenylalanine solution containing 3 g/dl of L-phenylalanine, 40 mg/dl of L-tyrosine, 100 mg/dl respectively of L-glutamic acid, L-alanine and L-lysine, 10 g/dl of NaCl and 2 g/dl of $Na_2SO_4$ was passed through a 1000 ml (80 cm height and 4 cm diameter bed) non-polar porous synthetic adsorbent, SP-207, according to a column system with a condition of SV=1, when L-phenylalanine was adsorbed selectively.

Then, the L-phenylalanine was eluted by 1 % (v/v) EtOH-0.2N NaOH aqueous solution (SV=2). The quantity of 1% (v/v) EtOH-0.2N NaOH aqueous solution required for the elution was 3.5l, and more than 98% of the L-phenylalanine adsorbed proved to be dluted.

By depositing crystals through neutralization by HCl after the concentration of the eluate, 80g of L-phenylalanine crystals not containig any L-tyrosine, etc. was obtained. The purity of these crystals was more than 99.5%, and no L-tyrosine or other amino acids were detected by T.L.C. analysis.

What is claimed is:

1. A process for refining phenylalanine, comprising:
   (i) contacting a solution containing phenylalanine and tyrosine as the main impurity with a non-polar, highly porous synthetic adsorbent having a greater affinity towards phenylalanine than towards tyrosine until substantially only phenylalanine has been adsorbed onto the said synthetic adsorbent;
   (ii) eluting phenylalanine adsorbed onto the said synthetic adsorbent; and
   (iii) recovering the said phenylalanine.

2. The process of claim 1, wherein the said non-polar, highly porous synthetic adsorbent is a styrenedivinylbenzene synthetic adsorbent.

3. The process of claim 2, wherein the said non-polar, highly porous adsorbent is selected from the group consisting of Diaion HP 10 to 50, SP-207, WAD-2, XAD-4 and mixtures thereof.

4. The process of claim 1, wherein the said process is run in a batch-wise manner.

5. The process of claim 1, wherein the said process is run in a column manner.

6. The process of claim 1, wherein the said process is run at a pH of from 3 to 9.

7. The process of claim 1, wherein the said process is run at a pH of from 5 to 6.

8. The process of claim 1, wherein the said process is run at a temperature of from 0° C. to 90° C.

9. The process of claim 1, wherein the said phenylalanine is eluted with a solvent, said solvent comprising water, an aqueous acid solution, an aqueous alkali solution, an aqueous lower aliphatic alcohol solution or a mixture thereof.

10. The process of claim 9, wherein the said lower aliphatic alcohol comprises methanol, ethanol or isopropyl alcohol.

* * * * *